United States Patent [19]

Fassbender

[11] Patent Number: 4,669,572
[45] Date of Patent: Jun. 2, 1987

[54] STETHOSCOPE

[75] Inventor: Nikolaus Fassbender, Bonn, Fed. Rep. of Germany

[73] Assignee: Firma Kirchner & Wilhelm, Stuttgart, Fed. Rep. of Germany

[21] Appl. No.: 858,052

[22] Filed: Apr. 30, 1986

[30] Foreign Application Priority Data

May 3, 1985 [DE] Fed. Rep. of Germany ... 8513039[U]

[51] Int. Cl.$^4$ ............................................. H04R 25/00
[52] U.S. Cl. ...................................... 181/137; 181/131
[58] Field of Search ................................. 181/131, 137

[56] References Cited

U.S. PATENT DOCUMENTS

| | | | |
|---|---|---|---|
| 3,035,656 | 5/1962 | Kebel | 181/137 |
| 3,193,047 | 7/1965 | Allen | 181/137 |
| 3,712,409 | 1/1973 | Kizakisz et al. | 181/137 |
| 4,569,413 | 2/1986 | Allen | 181/131 |

Primary Examiner—Benjamin R. Fuller

[57] ABSTRACT

An improved stethoscope having a reversible breastpiece comprises two base discs with an intermediate element relatively rotatable with respect thereto about the axis of the base discs to position its sound inlet channel with an outlet channel from the base discs. The channels in the base discs are arcuately spaced apart at extremes of relative rotational movement of the intermediate element. The sound inlet channel in the intermediate element, in turn, cooperates with nipples or fittings connected to the ear yoke. Means is provided to limit the amount of relative rotation of the intermediate element relative to the base discs, and positioning means is provided to releasably engage the intermediate element in a selected position of rotation against inadvertent misalignment. As can be seen, the several parts can be relatively easily fabricated with a high degree of precision and assembled in a fashion that enables optimal sound transfer from the selected one of the base discs.

16 Claims, 2 Drawing Figures

STETHOSCOPE

BACKGROUND OF THE INVENTION

The present invention relates to stethoscopes and, more particularly, to stethoscopes with a reversible breastpiece and in which a rotating element on the breastpiece selectively connects the ear yoke acoustically with either of the two sound receptors comprising the opposed faces of the breastpiece.

It is known to produce stethoscopes with such reversible breastpieces in which the rotating element provides a sound inlet channel which is connected in one position of rotation to the sound outlet channel of only the first sound receptor and in the other rotated position with that of only the second sound receptor. Although stethoscopes with such reversible or double sided breastpieces are known and offer significant advantages, the acoustics have frequently been relatively poor.

It is an object of the present invention to provide a novel stethoscope having a reversible breastpiece in which a rotating element selectively couples the ear yoke to one of the sound receptors and which provides improved acoustic properties.

It is also an object to provide such a stethoscope which may be readily assembled from a series of relatively simple components fabricated in a precise fashion and providing a durable and easily operated structure.

Another object is to provide such a stethoscope in which the rotatable element is positively located in either of its operative positions so as to ensure optimum sound transmission from the sound receptors to the ear yoke.

SUMMARY OF THE INVENTION

It has now been found that the foregoing and related objects may be readily attained in a stethoscope with a breastpiece operable on either of its surfaces, which includes a base member comprising a pair of axially spaced base discs defining a peripherally extending recess therebetween. A relatively rotatable member is disposed in the recess between the base discs and has radially extending surfaces closely adjacent the radially adjacent and opposed surfaces of the discs, and this rotatable member is mounted for relative rotation about the axis of the discs. An outlet fitting is provided on the relatively rotatable member for connection thereto of a tube connection to the associated ear yoke, and each of the base discs has an outlet channel opening at its radially extending opposed surface with the outlet channels of the discs being arcuately spaced apart. The relatively rotatable member has a sound inlet channel communicating with the outlet fitting to the ear yoke and alignable with one of the outlet channels of the discs in distinct rotated positions of the relatively rotatable member, whereby rotation of the relatively rotatable member will align the inlet channel with one of the outlet channels and transmit the sound therefrom to the ear yoke.

In the preferred embodiment, the rotatable member is of disc-like configuration, and the base member has a hub portion to define an annular channel between the radially adjacent surfaces of the discs. The relatively rotatable member is of annular configuration and is seated in the channel about the hub portion, and the axis of rotation is coaxial with the hub portion. This hub portion is conveniently provided by opposed, axially extending portions on each of the discs, and fastening means extends therethrough to assemble the discs and the rotatable member.

Generally, the base member discs includes a contact element mounted on its other radially extending surface for disposition against the surface of the object to be examined and to transmit the sound therethrough.

Most desirably, the stethoscope includes cooperating stop means on the relatively rotatable member and one of the base member discs for limiting rotation of the relatively rotatable member to end positions in alignment with the inlet channel and a desired one of the outlet channels. The stop means may comprise a projection on one of the relatively rotatable and the disc members, and an arcuate slot in the other cooperating member seating the projection. Moreover, the preferred stethoscope includes cooperating releasable latch means on the relatively rotatable member and one of the discs to releasably engage the relatively rotatable member in one of its relatively rotated positions. This latch means may include a detent on one of the cooperating members and a pair of accurately spaced recesses on the other cooperating member.

DETAILED DESCRIPTION OF THE ILLUSTRATED EMBODIMENT

Figure 1:
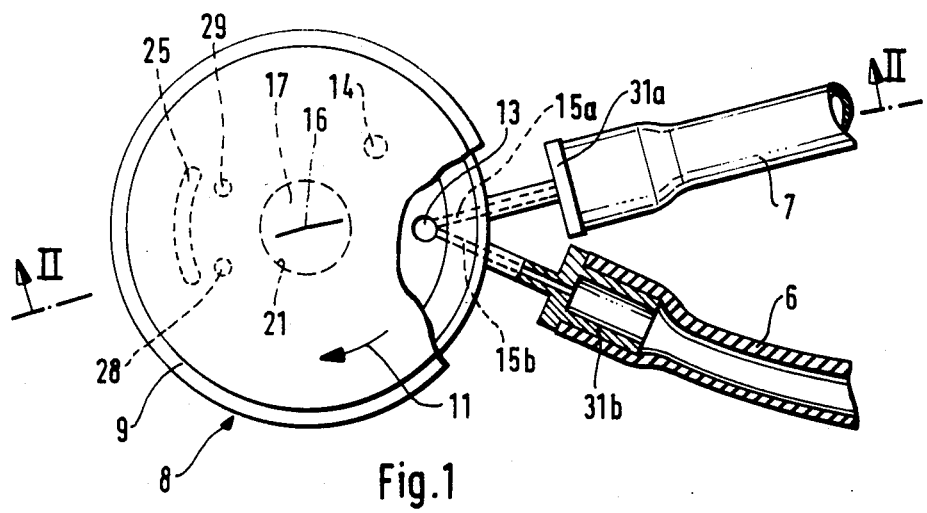
FIG. 1 is a fragmentary plan view of the breastplate and tubes of the ear yoke of a stethoscope embodying the present invention with portions broken away and in section to reveal internal construction.
Figure 2:
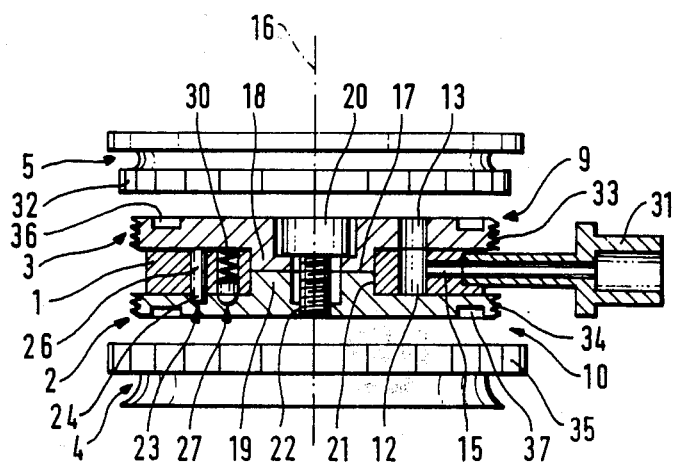
FIG. 2 is an exploded side elevational view of the stethoscope of FIG. 1 with the central portion of the assembly shown in section along the line II—II of FIG. 1.

Turning now in detail to the attached drawing, therein illustrated is a stethoscope embodying the present invention which includes a pair of contact elements generally designated by the numerals 4 and 5 providing the operative components to be placed against the surface of the object to be examined for the pickup of sound therefrom. As indicated in FIGS. 1 and 2, the contact elements 4 and 5 are of generally circular cross section but of different construction as will be pointed out more fully hereinafter.

Intermediate the contact elements 4 and 5 is a base member comprised of the base discs generally designated by the numerals 2 and 3 having opposed hub portions 18,19 which define an annular channel thereabout between the radially adjacent surfaces of the disc members 2,3. As can be seen in FIG. 2, the discs 2,3 are secured in assembly by a threaded fastener 20 seated in a recess in the base disc 3 and threadably engaged in a threaded aperture 22 in the base disc 2. The disc 2,3 are externally threaded as indicated by the numeral 33 and threadably mount thereon the internally threaded contact elements 4 and 5, respectively.

Rotatably seated in the channel between the disc 2,3 about their hub portions 18,19 is the rotatable disc member 1. As can be seen, the rotatable disc member 1 is of generally annular configuration and has its central aperture 21 dimensioned to seat closely against the hub portions 18,19, and its radial or side surfaces are closely seated against the opposed faces of the disc 2,3. It is, however, relatively freely rotatable between the discs 2,3 about the hub portions 18,19, and its axis of rotation 16 is through the fastener 20 and the axis of the discs 2,3. The plane of rotation is designated by the numeral 17 and is coincident with the plane of the abutting surfaces of the hub portions 18 and 19.

In the illustrated embodiment, the contact element 5 cooperates with the disc 3 to provide a sound receptor assembly generally designated by the numeral 9 of the diaphragm type, whereas the contact element 4 and the base disc 2 cooperate to provide a sound receptor assembly generally designated by the numeral 10 and of the funnel-type. The functional character of the two types of sound receptors is generally indicated by the outline of the contact elements 4,5. The diaphragm of the sound receptor 9 is held in the ring 32 thereof which is screwed onto the base disc 3. The sound receptor 10 is a contact funnel of suitably flexible material received in the ring 35 which in turn is screwed onto the base disc 2. Circumferential slots 36,37 are provided in the radially remote faces of the disc 2,3 adjacent the rings 32,35 and annular sealing elements (not shown) are seated therein to provide sealing between the two components when they are threaded into assembly.

The rotating element 1 has a vertically extending channel or passage 12 extending therethrough adjacent its periphery, and channels 15a and 15b extend outwardly therefrom to the outer circumference and provide recesses which seat the nipples 31a,31b which in turn seat thereon the flexible tubes 6,7 of the ear yoke (not shown). The base disc 3 has a vertically extending outlet channel 13 extending therethrough; as seen in FIG. 2, the channel 13 is coaxially aligned with the inlet channel 12 of the rotatable disc member 1 and this serves to effect transfer of sound from the sound receptor 9 to the ear yoke (not shown).

As seen in FIG. 1, the base disc member 2 has an outlet channel 14 which will be brought into coaxial alignment with the sound inlet channel 12 upon relative rotation of the rotatable disc member 1 and the discs 2,3, and this will produce transfer of sound from the sound receptor 10 to the ear yoke (not shown).

To limit the amount of relative rotation between the rotatable disc member 1 and the base discs 2 and 3, a pin 26 is seated in the rotatable disc member 1 and has a projecting portion 24 which slidably seats in an arcuate slot 25 formed in the base disc 2. The ends of the arcuate slot 25 and the diameter of the pin 26 are cooperatively configured and dimensioned so as to locate the sound inlet channel 12 with a selected one of the outlet channels 13,14 at the two extreme rotated positions. To releasably engage the rotatable disc member 1 in a selected relatively rotated position, a releasable detent ball generally designated by the numeral 27 is provided in an axially extending bore in the rotating element 1. The detent ball 27 is biased downwardly by the compression spring 30. In the radially adjacent surface of the base disc 2 are provided two arcuately spaced apart recesses 28,29 and dimensioned and configured to register with the spring loaded detent ball 27 in either of the extreme rotated positions. Although the latching mechanism will function to hold the members in the selected rotated position against inadvertent movement and provide the optimum sound transfer from the selected sound receptor, the latching force of the spring 30 can be readily overcome by applying sufficient rotational torque.

Thus, in the illustrated embodiment, there is provided means for ensuring positive coaxial alignment of the sound inlet channel of the relatively rotatable disc member with the selected one of the outlet channels of the sound receptors. Although not shown, bearings may be provided between the opposed surfaces to minimize frictional wear, although slight clearance can also be provided with minimal play between the opposed surfaces sufficient only to allow the relative rotation.

By providing close spacing of the outlets from the sound receptors and the inlet of the rotating element which communicates with the fitting for the ear yoke, sound loss can be minimized upon the precision alignment of the channels to facilitate maximum sound transfer therebetween.

In the illustrated embodiment of FIG. 1, the cross channel 15 shown in FIG. 1 comprises a pair of diverging channels 15a,15b communicating with a pair of nipples 31a,31b receiving a pair of tubes 6,7. Alternatively, a single channel 15 may be provided communicating with a single nipple 31 as schematically indicated in FIG. 2. The nipples 31 are usually secured in position in recesses within the rotatable disc member 1 by soldering or the like, and the tubes 6 and 7 are mounted thereon in frictional engagement in accordance with conventional practice.

The amount of rotation to effect a change from one sound receptor to the other can be relatively small, for example, only 30°. In one end position, the oscillating sound waves from the connected sound chamber of the selected sound receptor enter the sound inlet channel of the rotating element and brings into oscillation the air column to the ear yoke (or air columns in the case of a double-tube stethoscope). The flow connection from the sound channel of the inoperative sound receptor is automatically blocked by the rotatable disc member itself so that it does not adversely affect the sound being transmitted from the operative sound receptor.

As will be appreciated, neither of the sound receptors, i.e., the base discs and contact elements, should rotate with respect to the other during normal operation. Conveniently, this is effected by the threaded fastener extending through the hub portions of the base discs as shown in the illustrated embodiment. Alternatively, only one of the base discs may provide the hub portion to form the spacing of the annular channel therebetween, or a separate cylindrical element may be utilized to provide the spacer to define the channel therebetween, so long as the several elements are coupled in a fixed position relative to each other.

Thus, from the foregoing detailed specification and attached drawing, it can be seen that the stethoscope of the present invention provides highly effective sound transfer between either of two operative sound receptors and the ear yoke. The rotatable disc member can be positively positioned in axial alignment with the outlet channels of the selected sound receptor, and relative rotation is avoided.

Having thus described the invention, what is claimed is:

1. In a stethoscope with a brestpiece operable on either of its surfaces and having an ear yoke connected thereto, the combination comprising:
   (a) a base member comprising a pair of axially spaced base discs with opposed radially extending surfaces defining a recess therebetween extending about the periphery thereof;
   (b) a relatively rotatable memgber seated in said recess between said base discs and having radially extending surfaces closely adjacent said opposed radially extending surfaces of said discs, said rotatable member being mounted for relative rotation about the axis of said discs;

(c) an outlet fitting on said relatively rotatable member for connection thereto of a tube connection to the associated ear yoke, each of said baes discs having an outlet channel opening at its opposed radially extending surface, said outlet channels of said discs being arcuately spaced apart, said relatively rotatable member having a sound inlet channel communicating with the outlet fitting to the ear yoke and alignable with one of said outlet channels of said discs in distinct rotated positions of said relatively rotatable member, whereby rotation of said relatively rotatable member will align said inlet channel with one of said outlet channels and transmit the sound therefrom to the ear yoke.

2. The stethoscope in accordance with claim 1 wherein said rotatable member is of disc-like configuration.

3. The stethoscope in accordance with claim 1 wherein said base member has a hub portion to define an annular channel between said opposed radially extending surfaces of said discs and said relatively rotatable member is of annular configuration and is seated in said channel about said hub portion, said axis of rotation being coaxial with said hub portion.

4. The stethoscope in accordance with claim 3 wherein said hub portion is provided by opposed, axially extending portions on each of said discs, and fastening means extends therethrough to assemble said discs and said rotatable member.

5. The stethoscope in accordance with claim 2 wherein each of said base discs includes a contact element mounted on its surface opposed that defining said recess said contact element being adapted for disposition against the surface of the object to be examined and to transmit the sound therethrough.

6. The stethoscope in accordance with claim 1 wherein said stethoscope includes cooperating stop means on said relatively rotatable member and one of said base discs for limiting rotation of said relatively rotatable member to end positions in alignment with said inlet channel and a desired one of said outlet channels.

7. The stethoscope in accordance with claim 6 wherein said stop means comprises a projection on one of said relatively rotatable member and said base discs and an arcuate slot in the other cooperating member seating said projection.

8. The stethoscope in accordance with claim 1 wherein said stethoscope includes cooperating releasable latch means on said relatively rotatable member and one of said base discs to releasably engage said relatively rotatable member in one of said rotated positions.

9. The stethoscope in accordance with claim 8 wherein said latch means includes a detent on one of the cooperating members and a pair of accurately spaced recesses on the other cooperating member.

10. In a stethoscope with a breastpiece operable on either of its surface and having an ear yoke connected thereto, the combination comprising:
(a) a base member including a pair of axially spaced base discs and a hub portion to define an annular recess extending about its periphery between opposed radially extending surfaces of said discs;
(b) a relatively rotatable member of annular disc-like configuration seated in said recess between said base discs about said hub portion and having radially extending surfaces closely adjacent said opposed radially extending surfaces of said discs, said rotatable member being mounted for relative rotation about the axis of said discs which is coaxial with said hub portion;
(c) an outlet fitting on said relatively rotatable member for connection thereto of a tube connection to the associated ear yoke, each of said base discs having an outlet channel opening at its opposed radially extending surface, said outlet channels of said discs being arcuately spaced apart, said relatively rotatable member having a sound inlet channel communicating with the outlet fitting to the ear yoke and alignable with one of said outlet channels of said discs in distinct rotated positions of said relatively rotatable member, whereby rotation of said relatively rotatable member will align said inlet channel with one of said outlet channels and transmit the sound therefrom to the ear yoke.

11. The stethoscope in accordance with claim 10 wherein said hub portion is provided by opposed, axially extending portions on each of said base discs, and fastening means extends therethrough to assemble said discs and said rotatable member.

12. The stethoscope in accordance with claim 10 wherein each of said base discs includes a contact element mounted on its surface opposite that defining said recess, said contact element being adapted for disposition agsainst the surface of the object to be examined and to transmit the sound therethrough.

13. In a stethoscope with a breastpiece operable on either of its surfaces and having an ear yoke connected thereto, the combination comprising:
(a) a base member comprising a pair of axially spaced base discs with opposed radially extending surfaces defining a recess therebetween extending about the periphery thereof;
(b) a relatively rotatable member seated in said recess between said base discs and having radially extending surfaces closely adjacent said opposed radially extending surfaces of said discs, said rotatable member being mounted for relative rotation about the axis of said discs;
(c) an outlet fitting on said relatively rotatable member for connection thereto of a tube connection to the associated ear yoke, each of said base discs having an outlet channel opening at its opposed radially extending surface, said outlet channels of said discs being acruately spaced apart, said relatively rotatable member having a sound inlet channel communicating with the outlet fitting to the ear yoke and alignable with one of said outlet channels of said disc in distinct rotated positions of said relatively rotatable member, whereby rotation of said relatively rotatable member will align said inlet channel with one of said outlet channels and transmit the sound therefrom to the ear yoke; and
(d) cooperating stop means on said relatively rotatable member and one of said base discs for limiting rotation of said relatively rotatable member to end positions in alignment with said inlet channel and a desired one of said outlet channels.

14. The stethoscope in accordance with claim 13 wherein said stop means comprises a projection on one of said relatively rotatable member and said base discs and an arcuate slot in the other cooperating member seating said projection.

15. The stethoscope in accordance with claim 13 wherein said stethoscope includes cooperating releasable latch means on said relatively rotatable member and one of said base discs to releasably engage said relatively rotatable member in one of said rotated positions.

16. The stethoscope in accordance with claim 15 wherein said latch means includes a detent on one of the cooperating members and a pair of accurately spaced recesses on the other cooperating member.

* * * * *

UNITED STATES PATENT AND TRADEMARK OFFICE
CERTIFICATE OF CORRECTION

PATENT NO. :     4,669,572
DATED       :     June 2, 1987
INVENTOR(S) :    Nikolaus Fassbender It is certified that error appears in the above—identified patent and that said Letters Patent is hereby corrected as shown below:

Column 4, line 57, "brestpiece" should be -- breastpiece --;
          line 65, "memgber" should be -- member --.
Column 5, line 5, "baes" should be -- base --;
          line 34, "opposed" should be -- opposite --;
          line 61, "surface" should be -- surfaces --;
Column 6, line 30, "agsainst" should be -- against --;
          line 50, "acruately" should be -- arcuately --;
          line 54, "disc" should be -- discs --.

Signed and Sealed this

Twenty-seventh Day of October, 1987

Attest:

DONALD J. QUIGG

Attesting Officer

Commissioner of Patents and Trademarks